(12) United States Patent
Schneider

(10) Patent No.: US 9,138,004 B2
(45) Date of Patent: *Sep. 22, 2015

(54) CHLORAMINE T BASED TEAT CLEANER AND RELATED PROCESS

(75) Inventor: Charles A. Schneider, Villa Hills, KY (US)

(73) Assignee: H&S Chemical Company, Inc., Covington, KY (US)

( * ) Notice: Subject to any disclaimer, the term of this patent is extended or adjusted under 35 U.S.C. 154(b) by 2766 days.

This patent is subject to a terminal disclaimer.

(21) Appl. No.: 10/833,431

(22) Filed: Apr. 28, 2004

(65) Prior Publication Data

US 2004/0225017 A1 Nov. 11, 2004

Related U.S. Application Data

(60) Provisional application No. 60/467,920, filed on May 6, 2003.

(51) Int. Cl.
*A01N 33/14* (2006.01)
*A01N 41/06* (2006.01)
*C07C 303/36* (2006.01)
*A01N 59/00* (2006.01)

(52) U.S. Cl.
CPC ............... *A01N 59/00* (2013.01); *A01N 41/06* (2013.01)

(58) Field of Classification Search
CPC ....... A01N 41/06; A01N 59/00; A01N 25/02; C07C 303/36

USPC .......................................... 514/764, 708, 612
See application file for complete search history.

(56) References Cited

U.S. PATENT DOCUMENTS 6,123,953 A * 9/2000 Greff ............................ 424/407
6,296,841 B1 * 10/2001 Schneider ................... 424/76.1

OTHER PUBLICATIONS

Appel et al. (Wiener Tieraerztliche Monatsschrift (1988), 75(10), pp. 365-369).*

* cited by examiner

*Primary Examiner* — Shobha Kantamneni
(74) *Attorney, Agent, or Firm* — Richard M. Klein; Fay Sharpe LLP

(57) ABSTRACT

Dairy animals have been milked since prehistory. Because these dairy animals are often kept in confined areas the teat areas of these animals are often contaminated with bacteria. This invention is concerned with a process for sanitizing these contaminated teat areas by treating these areas with a solution of Chloramine T. The preferred solutions for sanitizing the teat areas have concentrations of from about 0.005 to about 1 weight percent. Treating solutions for use in this invention may further incorporate a coloring agents, wetting agent, surfactants, healing agents, dyes, thickening agents, skin conditioning agents, softeners etc. The process of this invention is fast acting and is effective against a wide spectrum of bacteria. After treatment the teat area of the dairy animal being milked is bacteria free and hence bacterial contamination of the milk, and Mastitis infections are eliminated.

12 Claims, No Drawings

CHLORAMINE T BASED TEAT CLEANER AND RELATED PROCESS

RELATED APPLICATIONS

This application claims priority of application Ser. No. 60/467,920 filed May 6, 2003.

FIELD OF THE INVENTION

The present invention relates to a process/procedures for sanitizing the teat area of an animal in the dairy arts. This invention is also concerned with a related compositions which are useful in sanitizing the teat area of a dairy animal. In a broad sense this invention comprises the application of a dilute solution of formulated Chloramine T to the teat area of a dairy animal prior to, and/or after the milking process. This invention is particularly suited for use on bovine teats.

BACKGROUND OF THE INVENTION

Animals have been milked by humans since prehistory. The animals in this instance represented a portable and renewable source for human nutrition. For millennia cows and goats have been the primary source for milk which is destined for human consumption. The milk produced by cows and goats is also highly advantageous as a source of food for human consumption, in that this milk can be readily converted to cheese which can be stored for long periods of time.

Because animals represented a significant food source these animals were very valuable property which the humans strived to protect. As humans continued to domesticate animals these animals become more reliant on humans for their protection. In its simplest terms a partnership was formed between the domesticated animals and humans. On the one hand the domesticated animals provided meat and milk for human consumption and in turn the humans provided protection for the domesticated animals. This partnership has served humans well.

In order to provide this protection humans, particularly at night, for thousands of years have confined animals to defined areas. These defined areas are referred to as paddocks. In modern terms these confining areas are referred to as dairy farms, barn yards or feed lots etc. Paddocks and these modem counterparts have one thing in common in that they expose the animals to high concentrations of fecal matter and urine both of which are bacterial laden.

When animals are confined they often lay in the confined areas in such a manner that the underside of the animal is in direct contact with a bacterial laden environment. Further since the udder and teats, here in after the teat area, of the animal is located on the underside of the animal this means that the teat areas of the animal is directly exposed to high concentration of harmful bacteria. As a result of this exposure the milk produced by the domesticated animals is almost always subject to bacterial contamination.

Naturally this bacterial contamination is undesirable in milk which is destined for human consumption. Chloramine T has been used as a biocide for over one hundred years, as a biocide Chloramine T has been used primarily in the purification of water.

Chloramine T is highly soluble in water. When Chloramine T is dissolved in water Cl+ ions are produced which are active against a wide range of bacteria and hence Chloramine T is an effective biocide.

Prior to May 6, 2002 Chloramine T was used on a limited basis to clean the teat areas of cows outside of the United States, but the present invention now provides a new, unobvious mechanism for sanitizing the teat area of a diary animal.

OBJECTS OF THE INVENTION

The primary object of this invention is a process whereby the teat areas of milk giving animals may be sanitized prior to milking.

Another object of this invention is to provide a very convenient, stable easily shippable, dry blend, non hazardous concentrate which replaces the current hazardous cumberson, DOT regulated teat dip formulas.

A further object is to provide a dry powdered formulated biocide for sanitizing the teat area of an animal prior to milking.

Still another object of this invention is a process whereby the teat area of an animal may be sanitized prior to milking without adversely affecting this area.

A further object is to provide a non staining method for sanitizing the teat area of dairy animals.

Still another object is a method for preventing mastitis in dairy animals.

SUMMARY OF THE INVENTION

The subject invention as defined by the appended claims relates to a process for sanitizing the teat area of a dairy animal in the milking process.

This invention relates to the application of solutions of formulated Chloramine T to the teat area of a dairy animal during the milking process.

Dairy animals are almost always kept in confined areas for at least part of the time. These confined areas are referred to by various terms i.e. paddock, barn yard, feed lot etc. As a result of this confinement, the teat area of the confined animals are often contaminated with urine and fecal matter. This contamination further adversely affects any milk produced by the confined dairy animals. Further this sequence of events in an undesirable and unhealthful situation, and can result in the dairy animal being affected with mastitis.

In accordance with this invention the teat area of the confined animals are treated with a sanitizing agent which comprises a solution of Chloramine T. Chloramine T is a known and effective biocide. Solutions of Chloramine T are effective against a wide range of bacteria.

DESCRIPTION OF THE PREFERRED EMBODIMENTS

Dairy animals and in particular cows have been milked for thousands of years. Because the teat area a dairy animal is located on its underside it is easily contaminated with bacteria. In the milking process this bacteria can easily contaminate the milk. In addition this bacteria can spread to the mammary tract of the udder causing infections which are referred to as mastitis. These infections can severely restrict the amount of milk produced by the dairy animal. Because cows are the most important dairy animals this application will be directed to the treatment of cows and the production of milk therefrom.

In the past few decades it has become common to sanitize the teats of a bovine prior to and after the milking process. The most common sanitizing agents sold and used are solutions of iodine compounds. While these iodine based solutions are effective in killing bacteria they have draw backs such as;

1. Iodine based compounds are hard on the tissue of the teat area.

2. Iodine based sanitizing solutions tend to stain the teat area and the hands and clothing of the operator.
3. Iodine based sanitizing solutions must be shipped in liquid form as an aqueous solution. This shipping of water substantially increases the shipping cost.
4. Iodine based sanitizing solutions are expensive.
5. Iodine based solutions are DOT regulated because they are considered corrosive.
6. The end user needs space to store large quanties of formula.
7. The end user has a problem in disposal of spent shipping containers used to transport the iodine based teat dips.

This invention provides an improved alternative to prior art. In the present invention the teat dip is provided as dry concentrate, activated by simply dissolving in tap water. Because of this the user can purchase; an economical product, that is cheap to transport and non hazardous. Further the product of this invention is easy to store, stable and compact and further the package containing active, formulation in accordance with this invention can be discarded in common trash. Lastly, the present invention provides a product that is kinder to the skin of both the treated animal and the dairyman.

This invention is concerned with a new process for sanitizing the teat area of a dairy animal with solutions of Chloramine T (hereinafter CHT).

In the prior art CHT has been used to kill bacteria and to sanitize various objects. This sanitization is usually effected with a dilute solution of CHT. Further in the prior art CHT has been used to kill bacteria in the cultured fish arts.

CHT further functions as a sanitizing agent by providing available Cl+ ions when it goes into solution. The Cl+ ion is a common sanitizing agent in the form of solutions which are generally referred to as bleach. Bleach is a solution of sodium hypochlorite. The Cl+ ion produced by bleach is very ionic and hence very harsh on animal tissue; therefore it is unsuitable for use as a teat cleaner.

In contrast the Cl+ ion produced by CHT is more covalent in nature and as such it is not harsh on animal tissue i.e. the skin of the teat area.

The process of this invention is effected by spraying, or otherwise treating the udder area of a bovine with a solution of CHT.

The process may be further effected by foaming the udder area in a formable solution of CHT.

The process may be further effected by dipping the teat area in a solution of CHT.

A broad range for the concentration of CHT used in the solution of this invention is from about 0.0005 to about 5 weight percent, with a more preferred range being from about 0.005 to about 1 weight percent, a most preferred range is from about 0.5 to about 1 weight percent. A most preferred concentration for CHT in solution for use in this invention is 0.5 weight percent.

The CHT solution for use in this invention may further include other substances such as coloring agents, wetting agents, surfactants, healing agents, dyes, thickening agents, skin conditioning agents and softeners. These additives facilitate the application of the CHT solution to the teat area and aid in keeping the bovine teat area healthy and in optimum condition for milk production.

While the CHT is usually applied as an aqueous formulated solution other solvents may be used.

CHT is highly soluble in water therefore solutions in accordance with this invention can be easily compounded. Because these solutions can be easily compounded the CHT can be shipped in dry powder form in pre measured packets. The shipment in dry powder form results in substantial savings in shipping cost as compared to the prior art iodine solutions which must be shipped as solutions.

The process of this invention effectively kills all bacteria as may be on the teat area of a bovine in less than one minute.

The process of this invention is further advantageous in that it leaves residual CHT on the teat area which inhibits future bacterial contamination. The residual CHT is to some degree in solution on the surface of the teat area due to the natural moisture content of the skin surface of the teat area. That is the residual CHT on the surface of the teat is to a degree dissolved by the moisture on the surface of the teat area. CHT is desirable in this situation as it naturally buffers out at a pH of about 9. At this pH the skin surface of the teat area not adversely affected. That is, solutions of CHT are particularly suited for sanitizing the teat area of animals as these solutions do not irritate the teat area.

In contrast to this desirable property for CHT, the prior art iodine based solutions tend to buffer out at a pH of about 1-2 which is well on the acidic side, at this acidic pH the surface of the teat becomes hard and calloused in a manner that the milking process is adversely affected. That is the prior art solutions irritate the teat area of living animals.

As is mentioned above solutions of CHT in accordance with this invention can incorporate a surfactant or a wetting agent. These surfactants are advantageous as they decrease the surface tension of the treating solution and hence allow the treating solution to completely wet out the teat area during the treating process. For use in this invention non ionic and anionic surfactants are preferred.

An example of a suitable anionic wetting agent for use in this invention is sold under the trademark Cacsoft-F-90 ( Sodium Linear anionic alkylbenzene Sulfonate.).

The concentration of the wetting agent can be from about .01 to about 5 percent, a more preferred range is 0.02 to about 3 percent. With a most preferred range being from 0.02 to about 0.1 percent. All percentages are weight percent.

Coloring agents may be added to color both post dip and pre dip solutions. These coloring agents change the color of the treating solution. By use of colored treating solutions the coverage of the treating solution during the treating process can be readily determined. Coloring agents are added to achieve a desired color. The concentration of the coloring agent is usually less than 1 percent, a suitable coloring agent is Graphtol 6825-3 Blue.

The concentration of thickening agents may vary with the thickening agent used. A preferred thickening agent for use in this invention is Cellosize HEC QR-100MH, as is sold by the Dow Chemical Company of Midland, Mich.

Other suitable thickening agents are; Polyox WSR which is thought to be poly ethylene oxide based. Further some hydroxyl methyl cellulose compounds have been found to be suitable thickening agents.

Softening agents or skin conditioning agents may also be added to keep the teat area in optimum condition for milking and milk production. A preferred skin conditioning agent is sorbitol such as sorbagem powder crystalline NF/FCC grade. Other suitable skin conditioning agents are glycerol (must be above 95% or above because of stability,) and lanolin.

EXAMPLES

The present invention is illustrated by the following examples. These examples are not to be construed as limiting the invention.

In the following examples Holstein dairy cows were brought into a milking parlor twice each day for varing length of test time (4 to 24 weeks) at a time. The teat areas of these cows were sprayed with a solution of Chloramine T having the defined concentration. (see examples 1 and 2) The Chloramine T solution was allowed to stand on the teat area for 1 to 5 minutes. At the end of the teat period the test animals were all observed with the indicated results.

Example No. 1

Dry formulated pouches A & B were dissolved in 55 gallons of water to produce 460 pounds of teat dip ready to apply.

| Pouch A contained: | |
| --- | --- |
| Chloramine T | 2.600 pounds |
| Coloring agent - Graphtol Blue Dye | 0.044 pounds |
| Surfactant- Calsoft F-90 | 0.110 pounds |
| Pouch B contained; | |
| Emolluent/Softener-Sorbitol powder | 2.200 pounds |

At the end of various time peaks between 4 and 16 weeks the teat areas of the cows were observed. No evidence of Mastitis was observed and the teat areas appeared to be normal and healthy

| Thickening agent- (Hydroxy ethyl cellulose) | 1.870 pounds |
| --- | --- |
| Coloring agent - Graphtol Blue Dye | 0.220 pounds |

Example 2

Dry formulated pouches A&B were dissolved in 55 gallons of water to produce 460 pounds of teat dip ready to apply to teats.

| Pouch A | |
| --- | --- |
| Chloramine T | 2.600 pounds |
| Coloring agent - Graphtol Blue Dye | 0.044 pounds |
| Surfactant- Sodium lauryl sulfate | 0.001 pounds |
| Pouch B | |
| Emolluent/Softener - Sorbitol powder | 2.200 pounds |
| Thickening agent - Hydroxyethyl cellulose | 1.870 pounds |
| Coloring agent - Graphtol Blue Dye | 0.220 pounds |

At the ends of various time periods between 4 and 16 weeks the teat areas of the cows were observed. No evidence of Mostitis was observed and the teat areas appeared to be normal and healthy.

What is claimed is:

1. A process for sanitizing the teat area of a dairy animal for milking which comprises:
   providing a mixture of Chloramine T, a coloring agent, and a skin conditioning agent;
   adding the mixture to water to form a solution, wherein the concentration of Chloramine T is less than about 5 weight percent of the solution, and wherein the solution has a pH of about 9; and
   applying the solution to the teat area of said animal in order to sanitize the teat area during milking without causing harmful side effects to the dairy animal.

2. The process of claim 1, wherein the concentration of Chloramine T, in said solution, is from about 0.0005 to about 5 weight percent.

3. The process of claim 1, wherein the concentration of Chloramine T, in said solution, is from about 0.005 to about 1 weight percent.

4. The process of claim 1, wherein the concentration of Chloramine T, in said solution, is from about 0.5 to about 1 weight percent.

5. The process of claim 1, wherein the concentration of Chloramine T, in said solution, is about 0.5 weight percent.

6. The process of claim 1 wherein the solution is applied prior to milking the animal.

7. The process of claim 1 wherein the solution is applied after milking the animal.

8. The process of claim 1 wherein the solution is applied both prior to and after milking the animal.

9. The process of claim 1 wherein the solution further incorporates an effective amount of a wetting agent.

10. The process of claim 9, wherein the concentration of the wetting agent in the solution is from about 0.01 to about 5 weight percent.

11. The process of claim 1, wherein the concentration of the coloring agent in the solution is less than 1 weight percent.

12. The process of claim 1, wherein the skin conditioning agent is selected from the group consisting of sorbitol, glycerol, and lanolin.

\* \* \* \* \*